(12) United States Patent
Steklenski et al.

(10) Patent No.: US 6,428,207 B1
(45) Date of Patent: *Aug. 6, 2002

(54) COMPUTER RADIOGRAPHIC ONCOLOGY PORTAL IMAGING

(75) Inventors: David J. Steklenski, Rochester; William E. Moore, Macedon, both of NY (US); Jeffrey W. Byng, Toronto (CA)

(73) Assignee: Eastman Kodak Company, Rochester, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/803,796

(22) Filed: Mar. 12, 2001

(51) Int. Cl.$^7$ ................................................ A61B 6/08
(52) U.S. Cl. ..................... 378/205; 250/484.4; 250/583
(58) Field of Search ............................ 250/484.4, 583

(56) References Cited

U.S. PATENT DOCUMENTS

| | | | |
|---|---|---|---|
| 4,368,390 A | | 1/1983 | Takahashi et al. |
| 4,977,327 A | * | 12/1990 | Arakawa et al. .......... 250/484.1 |
| 5,032,732 A | * | 7/1991 | Ito .......................... 250/484.1 |
| 5,138,171 A | * | 8/1992 | Tecotzky et al. .......... 250/484.1 |
| 5,427,868 A | | 6/1995 | Bringley et al. |
| 5,464,568 A | | 11/1995 | Bringley et al. |
| 5,712,486 A | * | 1/1998 | Soltani et al. ............ 250/484.4 |
| 5,871,892 A | | 2/1999 | Dickerson et al. |

OTHER PUBLICATIONS

Hammoudah MM. & Henschke, "Supervoltage Beam Films", International J. of Radiation Oncology, Biology, Physics, vol. 2, pp. 571–577, 1977.

D.A. Jaffray, JJ Battista, A. Fenster & PBE Munroe, X–ray Scatter in Megavoltage Transmission Radiography: Physical Characteristics and Influence on Image Quality, vol. 21, pp. 45–60, 1994.

R.T. Droege & B.E. Bjarngard, J. Medical Physics, "Metal Screen Film Detector MTF at Megavoltage X–ray Energies", vol. 6, pp. 515–518, 1979.

R.T. Droege & B.E. Bjarngard, J. Medical Physics, "Influence of Metal Screens on Contrast in Megavoltage X–ray Imaging"1 vol. 6, pp. 487–493, 1979.

B.A. Groh, L. Spies, B.M. Hesse & T. Bortfeld, "Scatter rejection methods in megavoltage imaging with an amorphous silicon flat panel array", SPIE, vol. 3977, 2000.

R.T. Droege & B.E. Bjarngard, "Metal Screen–film detector MTF at megavoltage X–ray energies" J. Medical Physics 6 (6), pp. 515–518, Nov./Dec. 1979.

J.C. Weiser, D. Gur & R.C. Gennari, "Evaluation of analog contrast enhancement and digital unsharp masking in low––contrast portal images", J. Medical Physics 17 (1), Jan./Feb. 1990 pp. 122–125.

H. Roehrig, W. Lutz, G. Barnea, G. Pond & W. Dallas, "Use of Computed Radiography For Portal Imaging" SPIE, vol. 1231 Medical Imaging OV: Image Formation (1990)pp. 492–497.

G. Barnea, E. Navon, A. Ginzburg & J. Politch, "Use of storage phosphor imaging plates in portal imaging and high–energy radiography: The intensifying effect of metallic screens on the sensitivity" J. Medical Physics 18 (3), May/Jun. 1991 pp. 432–438.

(List continued on next page.)

*Primary Examiner*—David P. Porta
*Assistant Examiner*—Elizabeth Gemmell
(74) *Attorney, Agent, or Firm*—J. Lanny Tucker

(57) ABSTRACT

Image storage assemblies comprise thin metal screens adjacent phosphor storage screens. The thin metal screen is from about 0.01 to about 0.75 mm in thickness when composed of copper and from about 0.05 to about 0.4 mm when composed of lead. These image storage assemblies can be used in portal imaging whereby imaging radiation is directed through the thin metal screens before the phosphor storage screens. Stimulating radiation can then be directed to the phosphor storage screen before it reaches the thin metal screen.

11 Claims, 1 Drawing Sheet

OTHER PUBLICATIONS

David Gur et al, "The Use of storage phosphors for portal imaging in radiation therapy: Therapists' perception of image quality", J. Medical Physics 16 (1), Jan./Feb. 1989 pp. 132–136.

R. M. Wilenzick & C.R.B. Merritt, "Megavoltage portal films using computed radiographic imaging with photostimulable phosphors", J. Medical Physics 14(3) May/Jun. 1987 pp. 389–392.

W.E. Moore & D.J. Steklenski, "Light–Weight Imaging Assemblies For Oncology Portal Imaging" U.S. 09/757,868 filed Jan. 10, 2001.

W.E. Moore & D.J. Steklenski, "Radiation Oncology Portal Imaging", U.S. 09/651,761 filed Aug. 31, 2000.

W–L A. Chen, A.P. Chipouras, T.A. Heath, W.A. Mruk, D.J. Steklenski, "Image Storage Phosphor Panels Having Flexible Supports", U.S. 09/667,150 filed Sep. 21, 2000.

* cited by examiner

# COMPUTER RADIOGRAPHIC ONCOLOGY PORTAL IMAGING

FIELD OF THE INVENTION

This invention is directed to radiography and in particular to image storage assemblies that are useful for oncology portal imaging. It also relates to radiation image recording and reproducing method. Thus, this invention is useful in portal radiography.

BACKGROUND OF TIE INVENTION

In conventional medical diagnostic imaging the object is to obtain an image of a patients internal anatomy with as little X-radiation exposure as possible. The fastest imaging speeds are realized by mounting a dual-coated radiographic element between a pair of fluorescent intensifying screens for imagewise exposure. About 5% or less of the exposing X-radiation passing through the patient is adsorbed directly by the latent image forming silver halide emulsion layers within the dual-coated radiographic element. Most of the X-radiation that participates in image formation is absorbed by phosphor particles within the fluorescent screens. This stimulates light emission that is more readily absorbed by the silver halide emulsion layers of the radiographic element.

Examples of radiographic element constructions for medical diagnostic purposes are provided by U.S. Pat. No. 4,425,425 (Abbott et al.) and U.S. Pat. No. 4,425,426 (Abbott et al.), U.S. Pat. No. 4,414,310 (Dickerson), U.S. Pat. No. 4,803,150 (Kelly et al.), U.S. Pat. No. 4,900,652 (Kelly et al.), U.S. Pat. No. 5,252,442 (Tsaur et al.), and *Research Disclosure*, Vol. 184, August 1979, Item 18431.

Radiation oncology is a field of radiology relating to the treatment of cancers using high energy X-radiation. This treatment is also known as teletherapy, using powerful, high-energy X-radiation machines (often linear accelerators) or cobalt (60) units to exposure the cancerous tissues (tumor). The goal of such treatment is to cure the patient by selectively killing the cancer while minimizing damage to surrounding healthy tissues.

Such treatment is commonly carried out using high energy X-radiation, 4 to 25 MVp. The X-radiation beams are very carefully mapped for intensity and energy. The patient is carefully imaged using a conventional diagnostic X-radiation unit, a CT scanner, and/or an MRI scanner to accurately locate the various tissues (healthy and cancerous) in the patient. With full knowledge of the treatment beam and the patient's anatomy, a dosimetrist determines where and for how long the treatment X-radiation will be directed, and predicts the radiation dose to the patient.

Usually, this causes some healthy tissues to be overexposed. To reduce this effect, the dosimetrist specifies the shape of the beam that will be controlled by lead blockers at the source or "port" of the treatment device. This effectively acts as a substantially opaque block in front of parts of the patient's body that absorbs X-radiation that would impact healthy tissues.

To this end, three distinct types of imaging are carried out in radiation oncology.

The first type of imaging is called "simulation". In this procedure, the patient is carefully imaged using a conventional diagnostic X-radiation unit, a conventional radiographic imaging film system, a storage phosphor system, or a digital system. In addition, a CT scanner and/or MRI scanner may be used to accurately locate the patient's anatomy. These procedures are essentially like those used in diagnostic radiography. They are carried out using from 80 to 150 kVp with low doses of radiation. These images provide detailed information on the patient's anatomy, and the location of the cancer relative to other body parts.

From the simulation images and/or CT/MRI data, a dosimetrist can determine where and for how long the treatment X-radiation should be directed. The dosimetrist uses a computer to predict the X-radiation dose for the patient. Usually this leads to some normal tissues being overexposed. The dosimetrist will introduce one or more "blocks" or lead shields to block X-radiation from normal anatomy. Alternatively, where available, the dosimetrist can shape the beam by specifying the positions for a multi-leaf collimator (MLC).

To determine and document that a treatment radiation beam is accurately aimed and is effectively killing the cancerous tissues, two other types of imaging are carried out during the course of the treatment. "Portal radiography" is generally the term used to describe such imaging. The first type of portal imaging is known as "localization" imaging in which the portal radiographic film is briefly exposed to the X-radiation passing through the patient with the lead shields removed and then with the lead shields in place. Exposure without the lead shields provides a faint image of anatomical features that can be used as orientation references near the targeted feature while the exposure with the lead shields superimposes a second image of the port area. This process insures that the lead shields are in the correct location relative to the patient's healthy tissues. Both exposures are made using a fraction of the total treatment dose, usually 1 to 4 monitor units out of a total dose of 45–150 monitor units. Thus, the patient receives less than 20 RAD's of radiation.

If the patient and lead shields are accurately positioned relative to each other, the therapy treatment is carried out using a killing dose of X-radiation administered through the port. The patient typically receives from 50 to 300 RAD's during this treatment.

A second, less common form of portal radiography is known as "verification" imaging to verify the location of the cell-killing exposure. The purpose of this imaging is to record enough anatomical information to confirm that the cell-killing exposure was properly aligned with the targeted tissue. The imaging film/cassette assembly is kept in place behind the patient for the full duration of the treatment. Verification films have only a single field (the lead shields are in place) and are generally imaged at intervals during the treatment regime that may last for weeks.

Portal radiographic imaging film, assembly and methods are described, for example, in U.S. Pat. No. 5,871,892 (Dickerson et al.) in which the same type of radiographic element can be used for both localization and portal imaging.

A radiographic phosphor panel contains a layer of phosphor, a crystalline material that responds to X-radiation on an imagewise basis. Radiographic phosphor panels can be classified, based on the type of phosphors, as prompt emission panels and image storage panels.

Intensifying screens are the most common prompt emission panels and are generally used to generate visible light upon exposure to provide an image in radiographic silver halide materials.

Storage phosphor panels comprise storage phosphors that have the capability of storing latent X-radiation images for later emission. Storage phosphors are distinguishable from the phosphors used in intensifying screens because the intensifying screen phosphors cannot store latent images for later emission. Rather, they immediately release or emit light upon irradiation. Various storage phosphors are described, for example in U.S. Pat. No. 4,368,390 (Takahashi et al.) and U.S. Pat. No. 5,464,568 (Bringley et al.).

Early use of storage phosphor systems for portal imaging used no metal converter screen. However, this adversely affects image quality as pointed out in several publications [for example, Wilenzink et al., *Med. Phys.*, 14(3), 1987, pp. 389–392, and David et al., *Med. Phys.*, 16(1), 1989, pp. 132–136 ].

Subsequent teaching in this art suggests that 1 mm copper metal plate would enhance contrast and image quality [for example, Weiser et al., *Med. Phys.* 17(1), 1990, pp. 122–125, and Roehrig et al., *SPIE*, 1231, 1990, pp. 492–497]. Soon thereafter, aluminum, copper, tantalum, and lead metal plates were considered with storage phosphor screens [Barnea et al., *Med. Phys.*, 18(3), 1991, pp. 432–438]. The tantalum metal plates were 0.4 mm thick to reach equilibrium at 6 MV. Thus, the conventional understanding in the art is that even storage phosphor panels require relatively thick metal screens to improve image quality. However, the weight of such image storage assemblies is considerable and creates a problem for users in the medical imaging community.

Since the earliest teaching about the need for metal screens in image storage assemblies, the thickness of the metal screens has been set at 1 mm or more when copper is used and at 0.6 mm when lead is used. It was consistently believed that thick metal screens were required to avoid overexposure especially for portal imaging.

Conventional image storage assemblies are illustrated in FIG. 1 (described in more detail below). A commercial imaging assembly of this type is used with the commercially available KODAK ACR 2000 system (Eastman Kodak Company).

Thus, conventional image storage assemblies provide the desired high contrast images, but because of the thick metal screens used to provide the desired imaging features, they are very heavy and difficult and unsafe to carry throughout medical facilities. Medical users have tolerated this disadvantage because it has been believed that the thick metal plates are necessary for desired imaging properties. We have found that this is not the case and it is to this problem that the present invention is directed.

SUMMARY OF THE INVENTION

The present invention provides a radiographic image storage assembly comprising a metal screen that is positioned adjacent to a phosphor storage screen, the metal screen having a thickness of from about 0.1 to 0.75 mm when composed of copper or a thickness of from about 0.05 to 0.4 mm when composed of lead.

This invention also provides a radiation image recording and reproducing method for localization comprising the steps of:

A) exposing a storage phosphor in a radiographic image storage assembly to reflected or transmitted radiation of a first wavelength to store the radiation within the storage phosphor,
   the radiographic image storage assembly comprising a metal screen that is positioned adjacent to a storage phosphor screen comprising the storage phosphor, the metal screen having a thickness of from about 0.1 to 0.75 mm when composed of copper or a thickness of from about 0.05 to 0.4 mm when composed of lead, and
   the radiographic image storage assembly positioned in relation to the exposing radiation of the first wavelength such that the exposing radiation passes through the metal screen before the storage phosphor, B) exposing the storage phosphor to radiation of a second wavelength to release the stored radiation as light emission of a third wavelength, the second wavelength radiation directed through the storage phosphor before it reaches the metal screen, and C) detecting the emitted light of the third wavelength.

This invention also provides a method (also known as verification) of confirming the targeting of X-radiation comprising:

A) positioning the radiographic image storage assembly described above to a region of a subject, B) directing the X-radiation at the region of the subject containing features that are identifiable by differing levels of X-radiation absorption and creating a first stored image of X-radiation penetrating the subject in the storage phosphor screen of the radiographic imaging assembly,
   the radiographic image storage assembly positioned in relation to the exposing X-radiation such that the exposing X-radiation passes through the metal screen before the storage phosphor, C) directing X-radiation at the region of the subject and creating a second stored image superimposed on the first image in the storage phosphor screen, D) exposing the storage phosphor screen to radiation of a second wavelength to release the stored images as a light emission of a third wavelength, the second wavelength radiation being directed to the storage phosphor before it reaches the metal screen, and E) detecting the emitted light of the third wavelength.

The present invention provides a means for portal imaging using a light-weight image storage assembly (or cassette) that has the desired imaging properties. It was a surprise to us that the thickness of the metal screen could be significantly reduced from 1 mm without any significant loss in imaging properties or photographic speed. This invention will allow users to achieve portal imaging with lightweight portal imaging systems that are safer and easier to handle.

In addition, the image storage assembly of this invention can be used in simulation imaging whereby the first imaging radiation is directed through the storage phosphor before it reaches the thin metal screen. Thus, the thin metal screen is considered to be in "back" of the storage phosphor layer for simulation imaging. The storage phosphor can then be stimulated by directing second radiation through the storage phosphor before it reaches the thin metal screen. Thus, one image storage assembly (or cassette) can be used in localization, verification, and simulation imaging.

DETAILED DESCRIPTION OF THE INVENTION

Definition of Terms:

The term "positioned adjacent" is used to define the positional relationship of the metal screen and the storage phosphor screen in the image storage assemblies of this invention. It refers to both screens being in intimate contact as well as the screens being separated by a gap of up to 3 mm. Such a gap can be created by an adhesive layer, air, or a compressible porous material.

The term "RAD" is used to indicate a unit dose of absorbed radiation, that is energy absorption of 100 ergs per gram of tissue.

The term "portal" is used to indicate radiographic imaging, films and intensifying screens applied to megavoltage radiotherapy conducted through an opening or port in a radiation shield.

The term "localization" refers to portal imaging that is used to locate the port in relation to the surrounding anatomy of the irradiated subject. Typically exposure times range from 1 to 10 seconds.

The term "verification" refers to portal imaging that is used to record patient exposure through the port during radiotherapy. Typically exposure times range from 30 to 300 seconds.

The terms "kVp" and "MVp" stand for peak voltage applied to an X-ray tube times $10^3$ and $10^6$, respectively.

The term "fluorescent intensifying screen" or "fluorescent screen" refers to a screen that comprises one or more phosphors that absorb X-radiation and immediately emit light.

The term "storage phosphor" refers to a phosphor that has the capacity of storing latent X-radiation images for later release.

The term "metal screen" refers to a metal screen that absorbs MVp level X-radiation to release electrons and absorbs electrons that have been generated by X-radiation prior to reaching the screen.

The terms "front" and "back" refer to features or elements nearer to and farther from, respectively, the object being exposed to X-radiation.

The term "rare earth" is used to indicate elements having an atomic number of 39 or 57 through 71.

*Research Disclosure* is published by Kenneth Mason Publications, Ltd., Dudley House, 12 North St., Emsworth, Hampshire P010 7DQ England.

The present invention is described in part by reference to the Figures.

Figure 1:
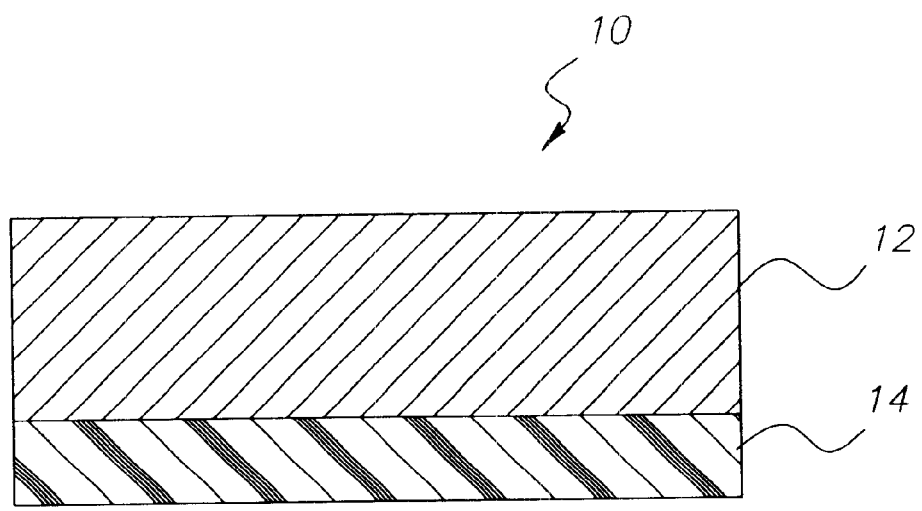
FIG. 1 is an enlarged cross sectional view of a conventional portal imaging assembly.

FIG. 1 illustrates a conventional portal imaging assembly 10 comprising a thick (at least 1 mm) metal sheet or plate (metal screen) 12 on the front side of storage phosphor screen 14. Examples of imaging assemblies include those provided with a KODAK ACR 2000 system.

Figure 2:
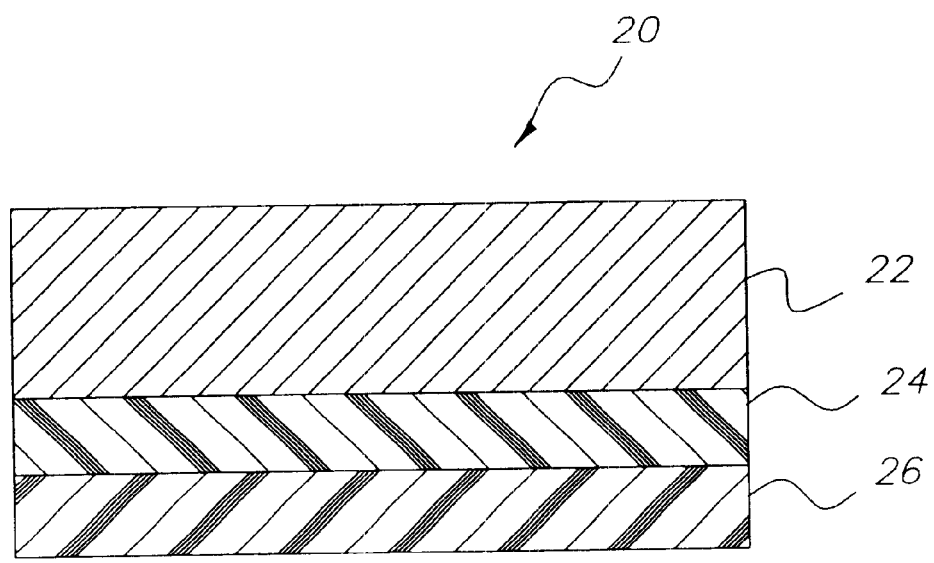
FIG. 2 is an enlarged cross sectional view of a portal imaging assembly of the present invention comprising a storage phosphor panel and a thin metal screen on the backside.

The advantages of the present invention are achieved by using much thinner metal screens particularly on the back side of the phosphor storage screen in the imaging assembly. The simplest arrangement is shown in FIG. 2 wherein imaging assembly 20 comprises thin (see below) metal screen 24, phosphor storage screen 22, and optional support 26.

During localization portal imaging the patient is briefly exposed to 4 to 25 MVp X-radiation over a region that is somewhat larger than the radiotherapy target area for the purpose of obtaining a discernible image of anatomy reference features outside the target area. This is immediately followed by a brief exposure through the port in the shields, to create an image of the port superimposed on the broader region first exposure. Total exposure during localization imaging is limited to 10 seconds or less, typically from 1 to 10 seconds. The object is to obtain an image that confirms or guides alignment of the port for radiotherapy, but to limit exposure to the Mvp X-radiation to the extent possible. By seeing in the image the location of the port in relation to reference anatomy features, the port can be more accurately aligned with the target area, if necessary, before the longer duration radiotherapy exposure begins.

The phosphor storage screens of the present invention can take any convenient conventional form. The storage phosphor layers can take any conventional form and can be disposed on a suitable flexible or rigid substrate or support material. For the highest attainable speeds, a white or reflective support, such as a titania or barium sulfate loaded or coated support is preferred. Particular reflective supports that offer a balance of speed and sharpness are described in U.S. Pat. No. 4,912,333 (Roberts et al.), incorporated herein by reference. Flexible supports are generally polymeric in nature and include common polyesters used in making photographic films, including polyesters, cellulose acetate, and polycarbonate films.

In some embodiments, the support materials are flexible laminate support having two or more flexible substrates that are laminated or otherwise adhered together, as described in copending and commonly assigned U.S. Ser. No. 09/667,150 (filed Sep. 21, 2000 by Chen et al.).

Various storage phosphors are known including those described in U.S. Pat. No. 5,464,568 (Bringley et al.), incorporated herein by reference. Such phosphors are divalent alkaline earth metal fluorohalide phosphors containing iodide and are the product of firing an intermediate, comprising oxide and a combination of species characterized by the following formula (1):

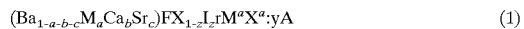
$$(Ba_{1-a-b-c}M_aCa_bSr_c)FX_{1-z}I_zM^aX^a:yA \tag{1}$$

wherein "M" is magnesium (Mg), calcium (Ca), strontium (Sr), or barium (Ba), "F" is fluoride, X" is chloride (Cl), or bromide (Br), "I" is iodide, $M^a$ is sodium (Na), potassium (K), rubidium (Rb), or cesium (Cs), $X^a$ is fluoride (F), chloride (Cl), bromide (Br), or iodide (I), "A" is europium (Eu), cerium (Ce), samarium (Sm), or terbium (Tb), "z" is $1 \times 10^{-4}$ to 1, "y" is from $1 \times 10^{-4}$ to 0.1, the sum of a, b and c is from 0 to 4, and r is from $10^{-6}$ to 0.1.

In another embodiment, the storage phosphor is produced by utilizing an oxosulfur reducing agent containing phosphor intermediate as described in U.S. Pat. No. 5,427,868 (Bringley et al.), incorporated herein by reference.

Other examples of suitable storage phosphors also include the various classes of materials described in U.S. Pat. No. 4,368,390 (Takahashi et al.), incorporated herein by reference, and including for example divalent europium and other rare earth activated alkaline earth metal halide phosphors and rare earth element activated rare earth oxyhalide phosphors. Of these types of phosphors, the more preferred phosphors include alkaline earth metal fluorohalide storage phosphors [particularly those containing iodide such as alkaline earth metal fluorobromoiodide storage phosphors as described in U.S. Pat. No. 5,464,568 (noted above)].

The phosphor layer(s) can comprise one or more phosphors that contain iodide in one or more of those layers. In particular, the alkaline earth metal phosphors can be the products of firing starting materials comprising optional oxide and a combination of species characterized by the following formula (2):

$$MFX_{1-z}I_zuM^aX^a:yA:eQ:tD \tag{2}$$

wherein "M" is magnesium (Mg), calcium (Ca), strontium (Sr), or barium (Ba), "F" is fluoride, "X" is chloride (Cl) or bromide (Br), "I" is iodide, $M^a$ is sodium (Na), potassium (K), rubidium (Rb), or cesium (Cs), $X^a$ is fluoride (F), chloride (Cl), bromide (Br), or iodide (I), "A" is europium (Eu), cerium (Ce), samarium (Sm), or terbium (Tb), "Q" is BeO, MgO, CaO, SrO, BaO, ZnO, $Al_2O_3$, $La_2O_3$, $In_2O_3$, $SiO_2$, $TiO_2$, $ZrO_2$, $GeO_2$, $SnO_2$, $Nb_2O_5$, $Ta_2O_5$, or $ThO_2$, "D" is vanadium (V), chromium (Cr), manganese (Mn), iron (Fe), cobalt (Co), or nickel (Ni). The numbers in the noted formula are the following: "z" is $1\times10^{31\ 4}$ to 1, "u" is from 0 to 1, "y" is from $1\times10^{-4}$ to 0. 1, "e" is from 0 to 1, and "t" is from 0 to 0.01 These definitions apply wherever they are found in this application unless specifically stated to the contrary. It is also contemplated that "M", "X", "A", and "D" represent multiple elements in the groups identified above.

Examples of particularly useful storage phosphors include SrS:Ce,SM, SrS:Eu,Sm, $ThO_2$:Er, $La_2O_2S$:Eu,Sm, ZnS:Cu,Pb, and the barium fluorohalides described in U.S. Pat. No. 5,464,568 (noted above).

The storage phosphors useful herein can be provided as particulate materials disposed within the binder, or in the form of particles encapsulated with a polymeric material (like a core-shell arrangement). Various polymeric shell materials include polyesters, nitrocellulose, polyalkyl acrylates and methacrylates, as well as vinyl epoxy resins described in U.S. Pat. No. 5,646,412 (Bryan et al.). A coupling agent can be used to facilitate the formation of the polymer shell directly onto the surface of the storage phosphor particles and to provide good adhesion between the two components.

A mixture of storage phosphors can be used, and particularly a mixture of storage phosphors containing iodide is useful. If more than one storage phosphor layer is used, those layers can be composed of the same or different storage phosphors and the same or different binders. The multiple phosphor layers can also have the same or different thickness. The amount of the one or more storage phosphors in the phosphor layers is generally at least 50 weight percent, and preferably from about 80 to about 98 weight percent, based on total dry layer weight.

The storage phosphor layers comprise one or more binders to give the layers structural coherence. In general, the binders useful in this invention are those conventionally used for this purpose in the art. They can be chosen from a wide variety of known organic polymers that are transparent to X-radiation, stimulating and emitted radiation. Binder materials commonly used for this purpose include but are not limited to, natural polymers such as proteins (for example gelatins), polysaccharides (such as dextrans), poly(vinyl acetate), ethyl cellulose, vinylidene chloride polymers, cellulose acetate butyrate, polyvinyl alcohol, sodium o-sulfobenzaldehyde acetal of poly(vinyl alcohol), chlorosulfonated poly(ethylene), a mixture of macromolecular bisphenol poly(carbonates), and copolymers comprising bisphenol carbonates and poly(alkylene oxides), aqueous ethanol soluble nylons, poly(alkyl acrylates and methacrylates) and copolymers of poly(alkyl acrylates and methacrylates and acrylic acid or methacrylic acid) and poly(vinyl butryal) and poly(urethanes) elastomers. Mixtures of binders can be used if desired. These and other useful binder materials are described in U.S. Pat. No. 2,502,529 (Luckey), U.S. Pat. No. 2,887,379 (Ralph et al.), U.S. Pat. No. 3,617,285 (Staudenmeyer), U.S. Pat. No. 3,300,310 (Kenneth et al.), U.S. Pat. No. 3,300,311 (Kenneth et al.), U.S. Pat. No. 3,743,833 (Martic et al.), U.S. Pat. No. 4,574,195 (Teraoka et al.), and in *Research Disclosure* Vol. 154, February. 1977, publication 15444 and Vol. 182, June. 1979.

Particularly useful binders are polyurethanes such as those commercially available as ESTANE polyurethanes from Goodrich Chemical Co., PERMUTHANE polyurethanes from Permuthane Division of ICI.

The binder(s) are present in the storage phosphor layers in an amount of at least 3 weight percent, and preferable from about 5 to about 12.5 weight percent, based on total phosphor dry weight.

Any conventional ratio of storage phosphor to binder can be used in the imaging assemblies of this invention. Generally thinner storage phosphor layers and sharper images are obtained when a high weight ratio of storage phosphor to binder is used. Preferably storage phosphor to binder weight ratios are in the range of from about 7:1 to about 30:1. More or less binder can be used if desired for specific applications.

The one or more storage phosphor layers can include other addenda that are commonly employed for various purposes, including but not limited to reducing agents (such as oxysulfur reducing agents), phosphites and organotin compounds to prevent yellowing, dyes and pigments for light absorption, plasticizers, dispersing aids, surfactants, and antistatic agents, all in conventional amounts.

The one or more storage phosphor layers generally have a total dry thickness of at least 50 $\mu$m, and preferably from about 100 $\mu$m to about 400 $\mu$m.

The phosphor storage screens of this invention preferably include a protective overcoat layer disposed on the outer storage phosphor layer. This layer is substantially clear and transparent to the light emitted by the storage phosphor and provides abrasion and scratch resistance and durability. It may also be desirable for the overcoat layer to provide a barrier to water or water vapor that may degrade the performance of the storage phosphor. Further, it may be desirable to incorporate components into the overcoat layer that prevent yellowing of the phosphor storage screen.

Many such materials are known in the art, including but not limited to, polyesters [such as poly(ethylene terephthalate)], polyethylene, polyamides, poly(vinyl butyral), cellulose esters (such as cellulose acetate), poly(vinyl formal), polycarbonates, vinyl chloride polymers, acrylic polymers [such as poly(methyl methacrylate) and poly(ethyl methacrylate)], and various polymer blends of fluorinated polymers and non-fluorinated polymers [such as blends of polyacrylates and vinylidene fluoride polymers. Mixtures of materials can be used if desirable. Other useful overcoat materials are described in U.S. Pat. No. 4,574,195 (Teraoka et al.), U.S. Pat. No. 5,401,971 (Roberts), U.S. Pat. No. 5,227,253 (Takasu et al.), U.S. Pat. No. 5,475,229 (Itabashi et al.), all incorporated herein by reference. The preferred materials are cellulose acetate, poly(vinylidene fluoride-co-tetrafluoroethylene), poly(vinylidene fluoride-co-chlorotrifluoroethylene), and blends of poly(vinylidene fluoride-co-tetrafluoroethylene), and poly[($C_{1-2}$ alkyl) methacrylate].

The protective overcoat may also be formed through the use of radiation curable compositions as those described in U.S. Pat. No. 5,149,592 (Wojnarowicz).

In addition to the film-forming polymer, the overcoat layer may contain a variety of agents designed to enhance its utility. Such agents include solid particulate materials or mattes as described in U.S. Pat. No. 4,059,768 (VanLandeghem et al.) and antistatic agents as described in U.S. Pat. No. 5,569,485 (Dahlquist et al.).

The protective overcoat layer can extend over the phosphor storage screen to seal the edges of the phosphor layer(s) or a separate seal may be applied using the same composition as that of the overcoat or a different composition.

While anticurl layers are not required, they are generally preferred in order to balance the forces exerted by the coating of the storage phosphor layer(s) and protective overcoat. Materials used to form anticurl layers include those identified above for use as binder materials or overcoat layer materials.

Subbing layers may be disposed between the support and the storage phosphor layer(s) is desired to enhance layer adhesion. Materials useful for this purpose are those conventionally used in subbing layers in photographic silver halide materials and are described for example in *Research Disclosure* Vol. 176, December. 1978, publication 17643 (Section XVII) and Vol. 184, August. 1979, publication 18431 (Section I).

The metal screens useful in this invention can take any convenient conventional form. While metal screens are most easily fabricated as thin foils, they are often mounted on radiation transparent backings to facilitate handling. Convenient metals for screen fabrication are in the atomic number range of from 22 (titanium) to 82 (lead). Metals such as copper, lead, tungsten, iron and tantalum have been most commonly used for metal screen fabrication with lead and copper in that order being the most commonly employed metals.

The metal screens used in the practice of this invention are thinner than conventional screens. They typically range from about 0.05 to 0.75 mm in thickness. A preferred thickness range is from about 0.1 to 0.75 mm for copper and from about 0.05 to about 0.4 mm for lead. Preferably, the thickness is from about 0.1 to about 0.6 mm for copper screens and from about 0.05 to about 0.3 mm for lead screens. Most preferred copper screens have a thickness of from about 0.1 to about 0.5 mm.

Instead of employing separate metal and storage phosphor screens, it is possible to integrate both functions into a single element by coating a storage phosphor layer onto a thin metal screen. Those metal screens would have the thickness within the ranges described above.

The imaging assemblies described herein can be packaged and/or used in a light-tight imaging article similar to those described for example in U.S. Pat. No. 5,871,892 (noted above, for example in Column 5). A commercial container of this type is available as KODAK DIRECTVIEW CR Cassette.

Details about preparing phosphor storage screens of this invention can be obtained from the teaching in U.S. Pat. No. 5,464,568 (noted above).

The image storage assemblies of the present invention are generally used by exposing the storage phosphor screen to X-radiation that has passed through the object (patient) being imaged. This radiation is passed through the thin metal screen before the storage phosphor layer, and is stored in an imagewise fashion in the storage phosphor layer(s). The storage phosphor screen is then scanned with suitable stimulating electromagnetic radiation (such as visible light or infrared radiation) to sequentially release the stored radiation as a light emission. The stimulating radiation is directed to the storage phosphor layer before it passes through the metal screen.

The emitted light can then be electronically converted to an image and either printed, stored, or transmitted elsewhere. Means for scanning, electronically converting the images, and printing or transmitting them elsewhere are well known. For example, KODAK ACR 2000 and CR 800 scanners and a KODAK CR 400 reader are suitable conventional means of this type.

In this way, portal imaging can be achieved using the image storage assemblies of this invention. The scanned images can be used, stored, or transmitted in any suitable manner.

The following examples are-illustrative of the present invention but the invention is not meant to be so limited.

EXAMPLE 1

Image Storage Assemblies

Image storage assemblies (cassettes, 14×17 inch, 35.6× 43.2 cm) of this invention were constructed using KODAK SO224 storage phosphor screens. Sheets of lead (0.125 mm, 0.250 mm, and 0.375 mm) were placed between the storage phosphor layers and the rigid supports associated with the storage phosphor screens.

A fourth image storage assembly (Control) was prepared using a 1 mm copper metal screen.

The four image storage assemblies were exposed to a source of $Ir^{192}$ and 6 Roentgens. Stimulating radiation was directed to the imaged assemblies. The three assemblies of the present invention provided similar desirable signals, but the Control assembly gave a smaller signal.

EXAMPLE 2

Scanning of Image Storage Assemblies

The imaging assemblies described in Example 1 were "erased" using the conventional "CR400 smart erase" feature. The original images in the phosphor layers were erased completely. A 0.25 mR exposure was then directed to each imaging assembly, followed by scanning using a conventional KODAK CR 400 reader. The results of scanned showed the 0.25 MR signal, but there was no evidence of the original images.

EXAMPLE 3

Portal Imaging

Using a conventional Varian, Inc. radiation therapy treatment machine, a 1.5-cm plastic patient tissue phantom was exposed through the "back" of each imaging assembly described in Example 1. A 10-cm plastic patient tissue phantom was on the front side of each imaging assembly. This provided calibrated exposures to each imaging assembly. Each of the imaging assemblies was exposed to 1 Rad, 3 Rads, 7 Rads, and 10 Rads in 10 cm square fields at the corners of the storage phosphor layers using 6 Mvp. We were surprised to observe that the 1-Rad signals in the storage phosphor layers behind each of the different lead screens were the same, ±3%. Surprisingly, the signal in the phosphor layer behind the copper screen (Control assembly) was 10% smaller.

The signal results in the imaging assemblies were the same for the other exposure levels. The imaging assemblies with the lead screens gave similar signals but the signal from the Control (copper) assembly was smaller by about 10%. This indicates that thinner copper and lead metal screens can be successfully used to provide the desired signals in the image storage assemblies.

EXAMPLE 4

Scanning of Image Storage Assemblies

The imaging assemblies exposed and evaluated in Example 3 were erased completely as described in Example 2. A 0.25 mR exposure was directed to each of the storage phosphors in the assemblies, and the resulting images were scanned using a conventional KODAK CR 400 reader. The scanned 0.25 mR images were seen but not the initial higher exposure.

EXAMPLE 5

Clinical Portal Imaging

A conventional RANDO phantom was exposed using 6 MVp X-radiation. Three image storage assemblies of this invention having different lead screens (0.125 mm, 0.250 mm, and 0.375 mm thickness) were used to record the images. One monitor unit was used for the large field and 1 additional monitor unit was used for the treatment field. All three imaging assemblies provided similar signals.

The images were scanned and manipulated with computer algorithms to increase contrast to a gamma of about 6. Unsharp masking using a 3 mm kernel and conventional KODAK EVP processing with 3 mm and 10 mm kernels were applied to the images. These images were then printed using a conventional KODAK 2180 laser printer and KODAK HeNe laser film. All of the images showed good detail.

EXAMPLE 6

Imaging Assembly with Copper Metal Screen

Two imaging assemblies were prepared similar to those described in Example 1 except that copper metal screens (0.5 and 0.25 mm) were used in place of lead screens. These imaging assemblies were exposed to a source of $Ir^{192}$ imaging radiation. Stimulating radiation was later directed to the imaged screens, thereby providing the desired signals.

The invention has been described in detail with particular reference to preferred embodiments thereof, but it will be understood that variations and modifications can be effected within the spirit and scope of the invention.

We claim:

1. A radiographic image storage assembly comprising a metal screen that is positioned adjacent to a storage phosphor screen, said metal screen having a thickness of from about 0.1 to 0.75 mm when composed of copper or a thickness of from about 0.05 to 0.4 mm when composed of lead.

2. The radiographic image storage assembly of claim 1 wherein said metal screen has a thickness of from about 0.1 to about 0.6 mm when composed of copper.

3. The radiographic image storage assembly of claim 2 wherein said metal screen has a thickness of from about 0.1 to about 0.5 mm when composed of copper.

4. The radiographic image storage assembly of claim 1 wherein said metal screen has a thickness of from about 0.05 to about 0.3 when composed of lead.

5. The radiographic image storage assembly of claim 1 wherein said storage phosphor screen comprises a support having thereon a storage phosphor layer comprising one or more phosphors that contain iodide, and is the product of firing starting materials comprising optional oxide and a combination of species characterized by the following formula (2):

$$MFX_{1-z}I_zuM^aX^a:yA:eQ:tD \qquad (2)$$

wherein "M" is magnesium (Mg), calcium (Ca), strontium (Sr), or barium (Ba), "F" is fluoride, "X" is chloride (Cl) or bromide (Br), "I" is iodide, $M^a$ is sodium (Na), potassium (K), rubidium (Rb), or cesium (Cs), $X^a$ is fluoride (F), chloride (Cl), bromide (Br), or iodide (I), "A" is europium (Eu), cerium (Ce), samarium (Sm), or terbium (Tb), "Q" is BeO, MgO, CaO, SrO, BaO, ZnO, $Al_2O_3$, $La_2O_3$, $In_2O_3$, $SiO_2$, $TiO_2$, $ZrO_2$, $GeO_2$, $SnO_2$, $Nb_2O_5$, $O_5,Ta_2$, or $ThO_2$, "D" is vanadium (V), chromium (Cr), manganese (Mn), iron (Fe), cobalt (Co), or nickel (Ni), "z" is $1\times10^{-4}$ to 1, "u" is from 0 to 1, "y" is from $1\times10^{-4}$ to 0.1, "e" is form 0 to 1, and "t" is from 0 to 0.01.

6. The radiographic image storage assembly of claim 1 wherein said storage phosphor screen comprises a support having thereon a storage phosphor layer comprising one or more phosphors that contain iodide and is a divalent alkaline earth metal fluorohalide phosphors characterized by the following formula (1):

$$(Ba_{1-a-b-c}M_aCa_bSr_c)FX_{1-z}I_zrM^aX^a:yA \qquad (1)$$

wherein "M" is magnesium (Mg), calcium (Ca), strontium (Sr), or barium (Ba), "F" is fluoride, "X" is chloride (Cl), or bromide (Br), "I" is iodide, $M^a$ is sodium (Na), potassium (K), rubidium (Rb), or cesium (Cs), $X^a$ is fluoride (F), chloride (Cl), bromide (Br), or iodide (I), "A" is europium (Eu), cerium (Ce), samarium (Sm), or terbium (Tb), "z" is $1\times10^{-4}$ to 1, "y" is from $1\times10^{-4}$ to 0.1, the sum of a, b and c is from 0 to 4, and r is from $10^{-6}$ to 0.1.

7. The radiographic image storage assembly of claim 6 wherein said phosphor layer comprising as a phosphor, SrS:Ce,SM, SrS:Eu,Sm, $ThO_2$:Er, $La_2O_2S$:Eu,Sm, or ZnS:Cu,Pb.

8. The radiographic image storage assembly of claim 1 wherein said storage phosphor screen comprises a flexible laminate support.

9. A radiation image recording and reproducing method comprising the steps of:

A) exposing a storage phosphor in a radiographic image storage assembly to reflected or transmitted radiation of a first wavelength to store said radiation within said storage phosphor,
  said radiographic image storage assembly comprising a metal screen that is positioned adjacent to a storage phosphor screen comprising said storage phosphor, said metal screen having a thickness of from about 0.1 to 0.75 mm when composed of copper or a thickness of from about 0.05 to 0.40 mm when composed of lead, and
  said radiographic image storage assembly positioned in relation to said exposing radiation of said first wavelength such that said exposing radiation passes through said storage phosphor screen before said metal screen, B) exposing said storage phosphor to radiation of a second wavelength to release said stored radiation as light emission of a third wavelength, the second wavelength radiation being directed through said storage phosphor before it reaches said metal screen, and C) detecting said emitted light of said third wavelength.

10. A method of confirming the targeting of X-radiation comprising:

A) positioning the radiographic image storage assembly of claim 1 to a region of a subject, B) directing the X-radiation at said region of said subject containing features that are identifiable by differing levels of X-radiation absorption and creating a first stored image of X-radiation penetrating said subject in the storage phosphor screen of said radiographic imaging assembly,
  said radiographic image storage assembly positioned in relation to said exposing X-radiation such that said exposing X-radiation passes through the metal screen before said storage phosphor, C) directing X-radiation at said region of said subject and creating a second stored image superimposed on said first image in said storage phosphor screen, D) exposing said storage phosphor screen to radiation of a second wavelength to release said stored images as a light emission of a third wavelength, said second wavelength radiation being directed to said storage phosphor before it reaches said metal screen, and E) detecting said emitted light of said third wavelength.

11. A radiation image recording and reproducing method comprising the steps of:

A) exposing a storage phosphor in a radiographic image storage assembly to reflected or transmitted radiation of a first wavelength to store said radiation within said storage phosphor, said radiographic image storage assembly comprising a metal screen that is positioned adjacent to a storage phosphor screen comprising the storage phosphor, said metal screen having a thickness of from about 0.1 to 0.75 mm when composed of copper or a thickness of from about 0.05 to 0.4 mm when composed of lead, and said radiographic image storage assembly positioned in relation to said exposing radiation of the first wavelength such that said exposing radiation passes through said metal screen before said storage phosphor, B) exposing said storage phosphor to radiation of a second wavelength to release said stored radiation as light emission of a third wavelength, the second wavelength radiation directed through said storage phosphor before it reaches said metal screen, and C) detecting said emitted light of the third wavelength.

* * * * *